(12) United States Patent
Schacher et al.

(10) Patent No.: US 8,147,777 B2
(45) Date of Patent: Apr. 3, 2012

(54) SAMPLE TUBE HOLDER

(75) Inventors: Gottlieb Schacher, Rotkreuz (CH); Ueli Stettler, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1110 days.

(21) Appl. No.: 11/643,639

(22) Filed: Dec. 21, 2006

(65) Prior Publication Data

US 2008/0025878 A1    Jan. 31, 2008

(30) Foreign Application Priority Data

Dec. 27, 2005    (EP) ..................................... 05077994

(51) Int. Cl.
*B01L 9/06*    (2006.01)
(52) U.S. Cl. ....................... 422/562; 422/526; 211/85.13
(58) Field of Classification Search .................. 206/558, 206/561–565; 220/485, 489, 495.03; 211/85.13; 422/526, 562
See application file for complete search history.

(56) References Cited

U.S. PATENT DOCUMENTS

| | | | |
|---|---|---|---|
| 2,593,794 A * | 4/1952 | Resina | 279/23.1 |
| 3,142,385 A | 7/1964 | Kahlenberg | |
| 3,352,427 A | 11/1967 | Lawrence et al. | |
| 3,819,194 A * | 6/1974 | Grevich et al. | 279/23.1 |
| 5,080,232 A | 1/1992 | Leoncavallo et al. | |
| 5,137,693 A * | 8/1992 | Mawhirt | 422/104 |
| 5,651,941 A | 7/1997 | Stark et al. | |
| 2004/0136869 A1* | 7/2004 | Itoh | 422/65 |
| 2004/0195193 A1 | 10/2004 | Jafari et al. | |
| 2005/0180896 A1 | 8/2005 | Itoh | |

FOREIGN PATENT DOCUMENTS

| | | |
|---|---|---|
| JP | 09-010605 | 1/1997 |
| JP | 09010605 | 1/2009 |

OTHER PUBLICATIONS

European Search Report dated Feb. 5, 2007.

* cited by examiner

*Primary Examiner* — In Suk Bullock
*Assistant Examiner* — Paul Hyun
(74) *Attorney, Agent, or Firm* — Dinsmore & Shohl LLP

(57) ABSTRACT

A sample tube holder for receiving and holding a sample tube having a cylindrical shape, a length symmetry axis and an outer diameter lying in a predetermined range. The sample tube holder comprises a solid body comprising at least one elongated chamber adapted for receiving a longitudinal portion of a sample tube, and an elastic element associated with and located outside of said chamber. When a sample tube is arranged in the chamber there is a gap between the sample tube and the side walls of the chamber, and the elastic element is in direct contact with at least three points of the outer surface of the sample tube, the elastic element thereby holds the sample tube and brings the length symmetry axis of the sample tube into coincidence with the length symmetry axis of the chamber.

34 Claims, 14 Drawing Sheets

US 8,147,777 B2

SAMPLE TUBE HOLDER

RELATED APPLICATIONS

This application claims priority to EP 05077994.1 filed Dec. 27, 2005.

FIELD OF THE INVENTION

The present invention relates generally to a sample tube holder, and in particular to a sample tube holder used in a clinical chemistry analyzer.

BACKGROUND OF THE INVENTION

A known sample tube holder used in clinical chemistry analyzer comprises a rectilinear array of chambers, each of which is adapted for receiving and holding in place a sample tube. All chambers of the array have the same shape and dimensions. The length symmetry axis of all chambers of the sample tube holder lie in one and the same plane, e.g. in a symmetry plane of the rectilinear array of chambers of the sample tube holder.

Primary sample tubes used in clinical chemistry analyzers usually have different diameters and usually also different lengths. In order to hold such primary sample tubes in place, each of the chambers of a known sample tube holder includes an elastic tongue which extends from the inner surface of a side wall of the chamber with an inclination towards the center thereof and which presses each sample tube against a side wall of the chamber. When several sample tubes having different diameters are inserted in respective chambers of such a sample tube holder, the length symmetry axis of the sample tubes are not aligned and lie at different distances from the plane which contains the length symmetry axis of the chambers of the sample tube holder. Sample tubes having a diameter close to the inner diameter of the chambers of the sample tube holder where they are inserted are approximately centered in those chambers, whereas the centers of smaller sample tubes clearly lie out of the centers of the chambers where they are inserted.

In another known sample tube holder the side walls of each of the chambers of the sample tube holder include four elastic tongues with an angular spacing of 90 degrees between them and these tongues press the sample tube towards the length symmetry axis of the chamber. Although centering of the sample tube can be in principle achieved in this way, in practice however manufacturing tolerances and non-uniform deformation of the tongues with time makes it impossible to ensure that each of the sample tubes inserted in the chambers of the known sample tube holder is accurately centered and that the length symmetry axis of all sample tubes inserted in the sample tube holder are accurately aligned and lie in the symmetry plane of the sample tube holder.

For the reasons indicated above, the prior art sample tube holders described above are not suitable for use in an analyzer where it is necessary that every one of the sample tubes is accurately centered in a chamber of the sample tube holder and that the length symmetry axis of all sample tubes inserted in the sample tube holder are accurately aligned and lie in the symmetry plane of the sample tube holder. This is for instance required if the sample tube holder is used in an analyzer having an automatic pipetting unit which moves the pipetting needle only along a rectilinear path which lies in the symmetry plane of the array of chambers of the sample tube holder. An accurate centering of every one of the sample tubes is also required to ensure that they are properly gripped by the gripper of a robotic device used for transporting the sample tubes.

SUMMARY OF THE INVENTION

It is against the above background that the present invention provides a sample tube holder for use in a clinical chemistry analyzer wherein each chamber of the holder is configured to accurately center sample tubes of different diameters so that a length symmetry axis of each sample tube inserted in a chamber of the sample tube holder coincides with the length symmetry axis of the chamber of the sample tube holder in which the sample tube is positioned, and thereby the length symmetry axis of all sample tubes in the sample holder are aligned and lie in a plane which contains the length symmetry axis of all the chambers of the sample tube holder.

Some of the noted advantages obtained with a sample tube holder according to the invention, for example and not limited thereto, are that it provides a low cost means for positioning sample tubes having different diameters in chambers of the sample tube holder and for accurately centering each sample tube in the chamber of the sample tube holder where the sample tube is inserted. The present invention also contributes to reduce the manufacturing cost of the analyzer by making possible use of a low cost automatic pipetting unit which moves the pipetting needle only along a rectilinear path which lies in the symmetry plane of the array of chambers of the sample tube holder, instead of e.g. a more expensive automatic pipetting unit which moves the pipetting needle in three directions (X, Y, Z) orthogonal to each other. A further noted advantage of a sample tube holder according to the invention is that the elastic elements it uses for holding the sample tubes do not undergo any deformation with time and therefore ensure an accurate centering of the sample tubes.

These and other features and advantages of the present invention will be more fully understood from the following description of various embodiments of the invention taken together with the accompanying drawings.

DETAILED DESCRIPTION OF THE INVENTION

Figure 1:
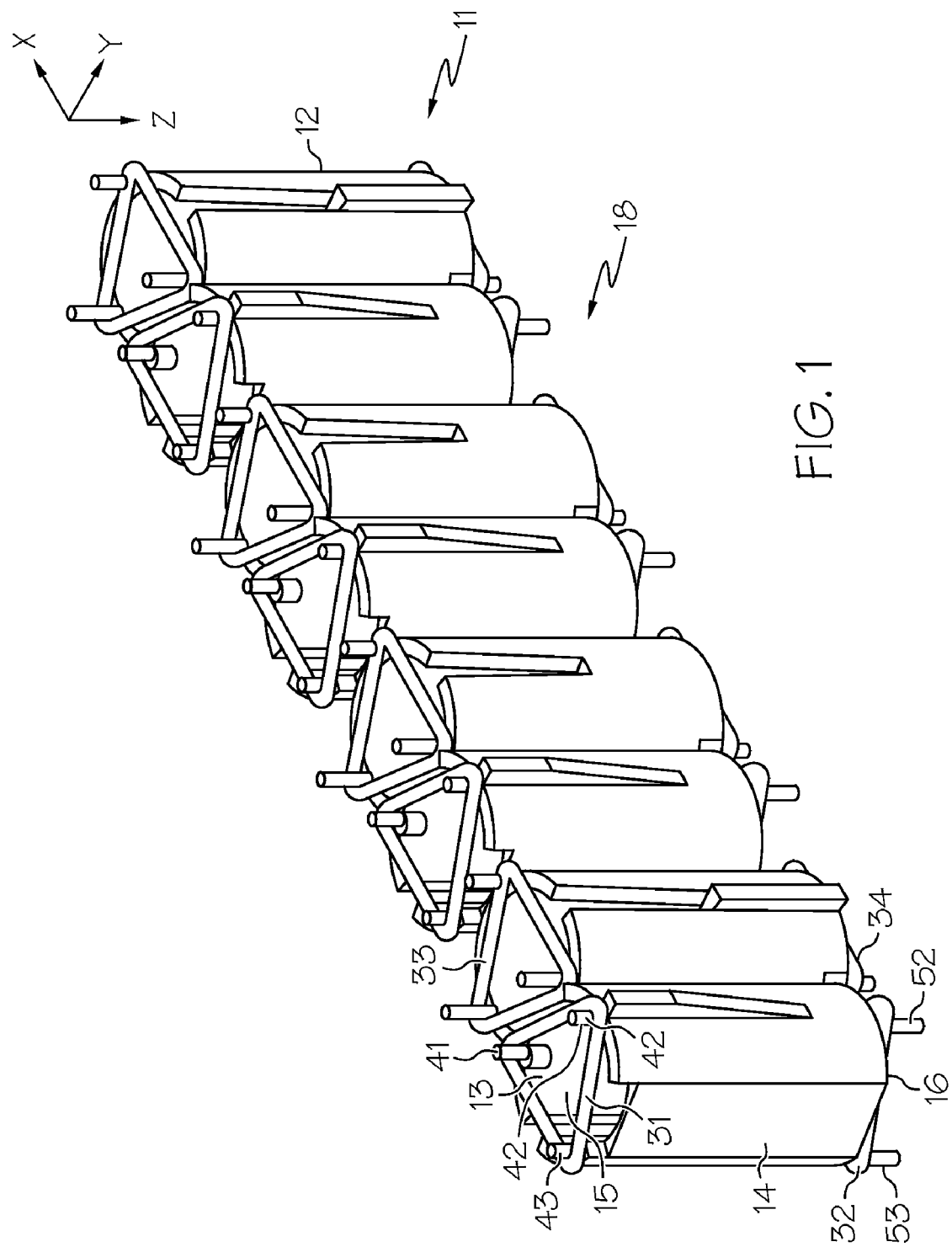
FIG. 1 shows a perspective view of an embodiment of a sample tube holder according to the present invention.

Reference will now be made in detail to several embodiments of a sample tube holder according to the invention that are illustrated in the accompanying drawings. These embodiments are set forth for the purpose of illustrating and aiding in the understanding of the invention, and are not to be construed as limiting. Wherever possible, same or similar reference numerals are used in the drawings and the description to refer to same or like parts. The drawings are in simplified form and may not be to precise scale. For purposes of convenience and clarity only, directional terms, such as, top, bottom, left, right, up, down, over, above, below, beneath, rear, back, front, horizontal, and vertical may be used with respect to the accompanying drawings.

Several embodiments of a sample tube holder 11 according to the invention are described hereinafter with reference made first to FIGS. 1 to 10. Such a sample tube holder 11 is adapted for receiving and holding a plurality of sample tubes 21 having a cylindrical shape and outer diameters lying in a predetermined range, e.g. in a range from about 11 to about 16 millimeters or in a range from about 7 to about 17 millimeters. Each of sample tubes 21 has a length symmetry axis 23 (see FIG. 8).

As shown by FIG. 1, one embodiment of a sample tube holder 11 according to the invention comprises a solid body 12 defining a rectilinear array of elongated chambers 13 and elastic elements such as, for example, garter springs 31, 32 associated with and located outside of each chamber 13 of the array. In other embodiments, any type of an elastic element may be used which is capable of sustaining stress without permanent deformation, thereby tending to return to its original shape or state (i.e., resting state) when the applied stress is removed, such as and not limited to, an elastic band, cord, or string, a metal or plastic clip, an o-ring, elastic fiber, and the likes. Solid body 12 comprises at least one chamber 13 and corresponding garter springs 31, 32 associated therewith. The description hereinafter applies to embodiments comprising a plurality of chambers 13 and to embodiments comprising at least one chamber 13. In the latter case, the description referring to each chamber 13 of an array of chambers applies also to a single chamber 13.

In one embodiment, solid body 12 is made by injection molding of a suitable plastic material.

Elastic elements 31 and 32 are adapted for centering each sample tube 21 arranged in a chamber so that the length symmetry axis 23 of the sample tube coincides with the length symmetry axis 17 of the chamber 13. Chambers 13 have each the same shape and dimensions. Each chamber 13 has side walls 14, an upper opening 15, an opposed lower opening 16, and a length symmetry axis 17 (see FIG. 8). Each chamber 13 is adapted for receiving a longitudinal portion of a sample tube 21.

In the embodiment shown by FIG. 1, solid body 12 comprises for each of chambers 13 a first array of pins, e.g. pins 41, 42, 43 in FIG. 1, which in one embodiment are e.g. rigid longitudinal projections of the side walls 14 of chamber 13 and extend away or upwards, and in other embodiments, may be pins of a similar or different material, such as a metal, an alloy, wood, composites, etc., provided to or formed with the side walls 14. In the illustrative embodiment, garter spring 31 is stretched around the first array of pins 41, 42, 43.

In another embodiment, solid body 12 further comprises for each of chambers 13 a second array of pins, e.g. pins 51, 52, 53 in FIG. 1, which in one embodiment are e.g. rigid longitudinal projections of the side walls 14 of chamber 13 and extend away or downwards, and in other embodiments, may be pins of a similar or different material, such as a metal, an alloy, wood, composites, etc., provided to or formed with the side walls 14. In the illustrative embodiment, garter spring 32 is stretched around the second array of pins 51, 52 and 53.

Garter springs 31, 32 are thus arranged with some prestressing around the above mentioned first and second array of pins, respectively.

In the above described configuration garter springs 31, 32 exert equal radial forces on angularly equidistant points of the outer surface of a sample tube inserted in a chamber 13. Connecting the ends of a garter spring can be accomplished in several ways; interlocking the end loops, tapering one end and screwing into the opposite end, soldering, or using another short extension spring as a connector by screwing it into both ends of the spring body.

Figure 3:
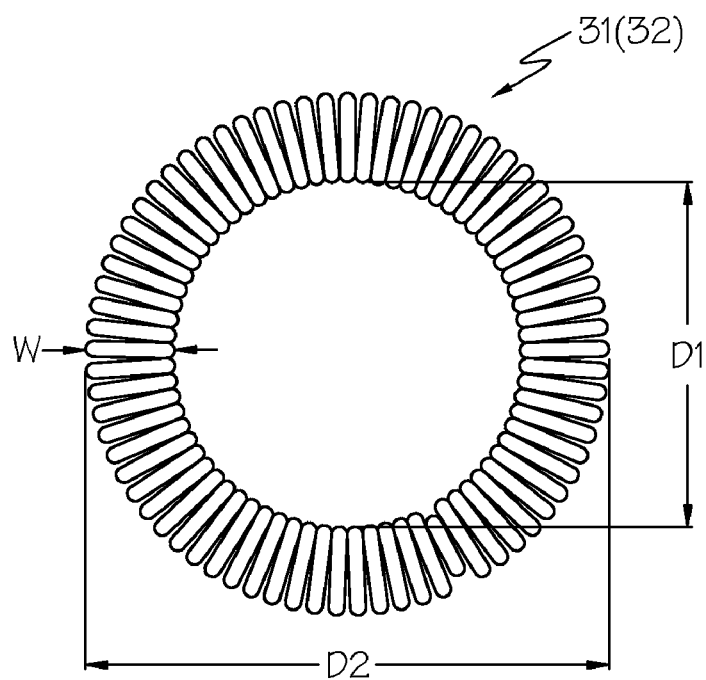
FIG. 3 shows a top view of each of garter springs 31 and 32 in a resting state.

FIG. 3 shows a top view of each of garter springs 31 and 32 in their resting states. As shown by FIG. 3, garter spring 31 (respectively 32) is a thin coil spring with ends joined to form a ring. In one embodiment, garter springs 31, 32 are made of stainless steel and in other embodiments may be a material selected from other metals, alloys, and plastics. In one embodiment, each of the garter springs 31, 32 has a body which has a width W lying in a range from about 1.5 to about 2.0 millimeters.

In one embodiment, the centers of the first array of pins 41, 42, 43 are located at the corners of a first regular polygon and centers of the second array of pins 51, 52, 53 are located at the corners of a second regular polygon.

In one embodiment, the corners of the first regular polygon and the corners of the second regular polygon lie on a first circle 44 (see FIG. 2) in a plane normal to the length symmetry axis 17 of chamber 13. The center of the first circle 44 lies on the length symmetry axis 17 of chamber 13, and the first circle 44 has a surface which is larger than the cross-section of chamber 13.

Figure 2:
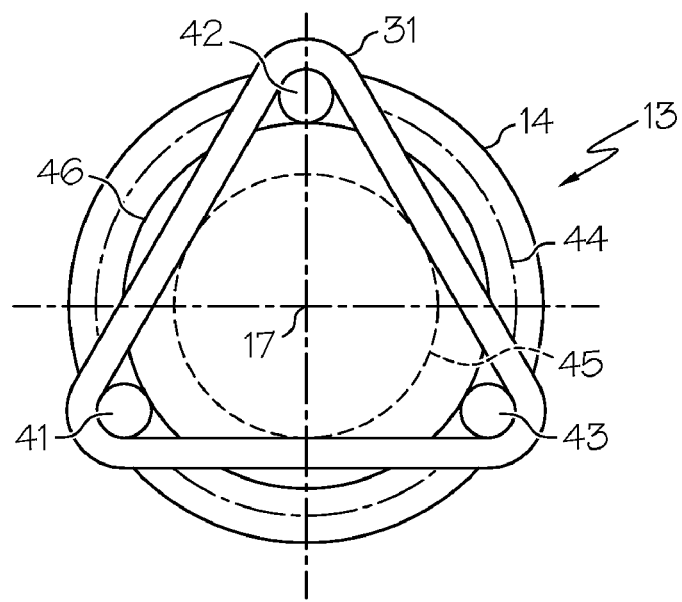
FIG. 2 shows a top view of a chamber 13 and a garter spring 31 of the sample tube holder 11 shown in FIG. 1.

As shown by FIG. 2, the inner sides of garter spring 31 stretched around pins 41, 42, 43 define a regular polygon, e.g. an equilateral triangle. In one embodiment, the diameter of a second circle 45, inscribed in the latter regular polygon, is smaller than the smallest outer diameter of a sample tube 21 to be inserted in a chamber 13 of the sample tube holder. For instance, if the smallest outer diameter of a sample tube 21 to be inserted in a chamber 13 is 11 millimeters, the second circle 45 has a diameter smaller than 11 millimeters, and if the smallest outer diameter of a sample tube 21 to be inserted in a chamber 13 is 7 millimeters, the second circle 45 has a diameter smaller than 7 millimeters.

The above description with reference to garter spring 31 also applies to garter spring 32 (not shown by FIG. 2) and the corresponding pins 51, 52, 53.

Figure 5:
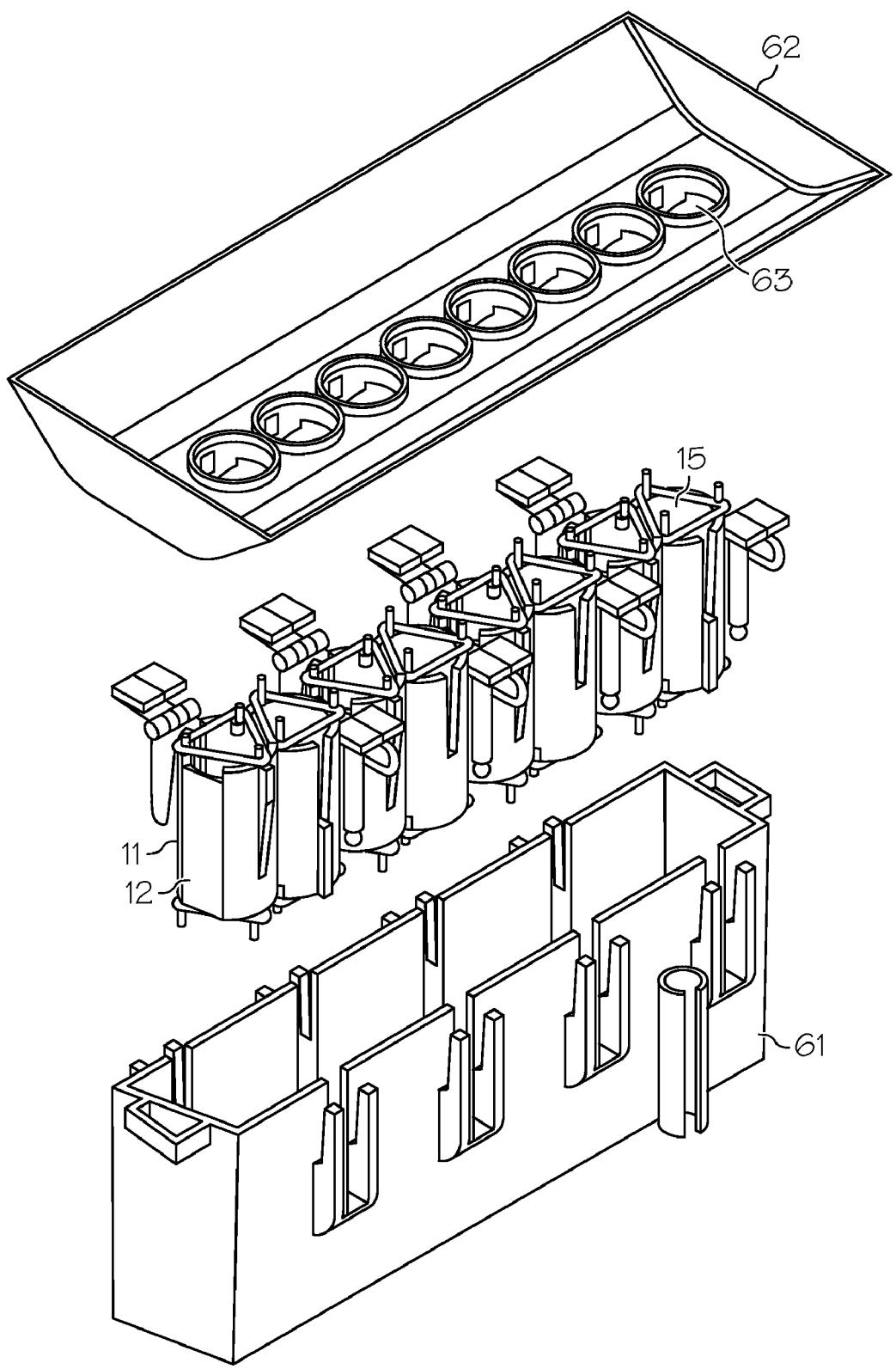
FIG. 5 shows an exploded perspective view of components of a sample tube holder assembly comprising the sample tube holder 11 shown in FIG. 1.

In one embodiment, each of the above mentioned regular polygons is an equilateral triangle as shown in FIGS. 1, 2 and 5, and in other embodiments may be any other suitable polygon that provides the above mentioned holding and centering feature of the present invention to an suitably shaped chamber, such as, for example, an elastic element situated around four pins that are provided centrally along the sides of a squared shaped chamber, or even an elastic element situated around three pins that are provided centrally along the sides of a triangle shaped chamber.

In the illustrative embodiment shown by FIG. 2, the centers of pins 41, 42, 43 of the first array of pins as well as the centers of pins 51, 52, 53 of the second array of pins (not shown in FIG. 2) are located at the corners of an equilateral triangle and these corners lie on a first circle 44 in a plane normal to the length symmetry axis 17 of chamber 13, the center of circle 44 lies on the length symmetry axis 17 of chamber 13.

In one embodiment, each of the above mentioned pins 41, 42, 43, 51, 52, 53 has a cylindrical shape and a diameter of e.g. 2 millimeters, and in other embodiments may be any other suitable geometric shape and diameter to retain an elastic element there around and to provide the above described retention and centering force to the elastic element.

FIG. 2 also shows side wall 14 of chamber 13 and a circle 46 which represents the inner surface of side wall 14 of chamber 13. The diameter of circle 46 determines the maximum diameter a sample tube insertable in chamber 13 may have. In the embodiment described above with reference to FIG. 2, circle 46 has a diameter of 16.3 millimeters and the largest diameter of a sample tube insertable in a chamber 13 of that embodiment is 16.2 millimeters.

As shown by FIG. 2, first circle 44 has a surface which is larger than the cross-section of chamber 13 defined by the surface of circle 46.

As shown by FIG. 2, the inner sides of garter spring 31 extend along the sides of an equilateral triangle. FIG. 2 shows a circle 45 inscribed in the latter triangle. The sample tube holder 11 according to the invention is suitable for holding sample tubes having an outer diameter that is larger than the diameter of circle 45. In other words the diameter of circle 45 is smaller than the smallest outer diameter of a sample tube 21 to be inserted in a chamber 13 of sample tube holder 11.

FIG. 3 shows the shape of each of garter springs 31 and 32 in their resting states. As shown by FIG. 3, each of these springs has an inner diameter D1, an outer diameter D2 and a width W. The latter inner diameter D1 is smaller than the diameter of first circle 44 in FIG. 2.

In one embodiment, garter springs 31 and 32 have a width W of e.g. 1.65 millimeters, and in other embodiments may have any suitable width W which provides the above described retention and centering force to the elastic element when situated around pins of a suitable chamber according to the present invention.

Figure 4:
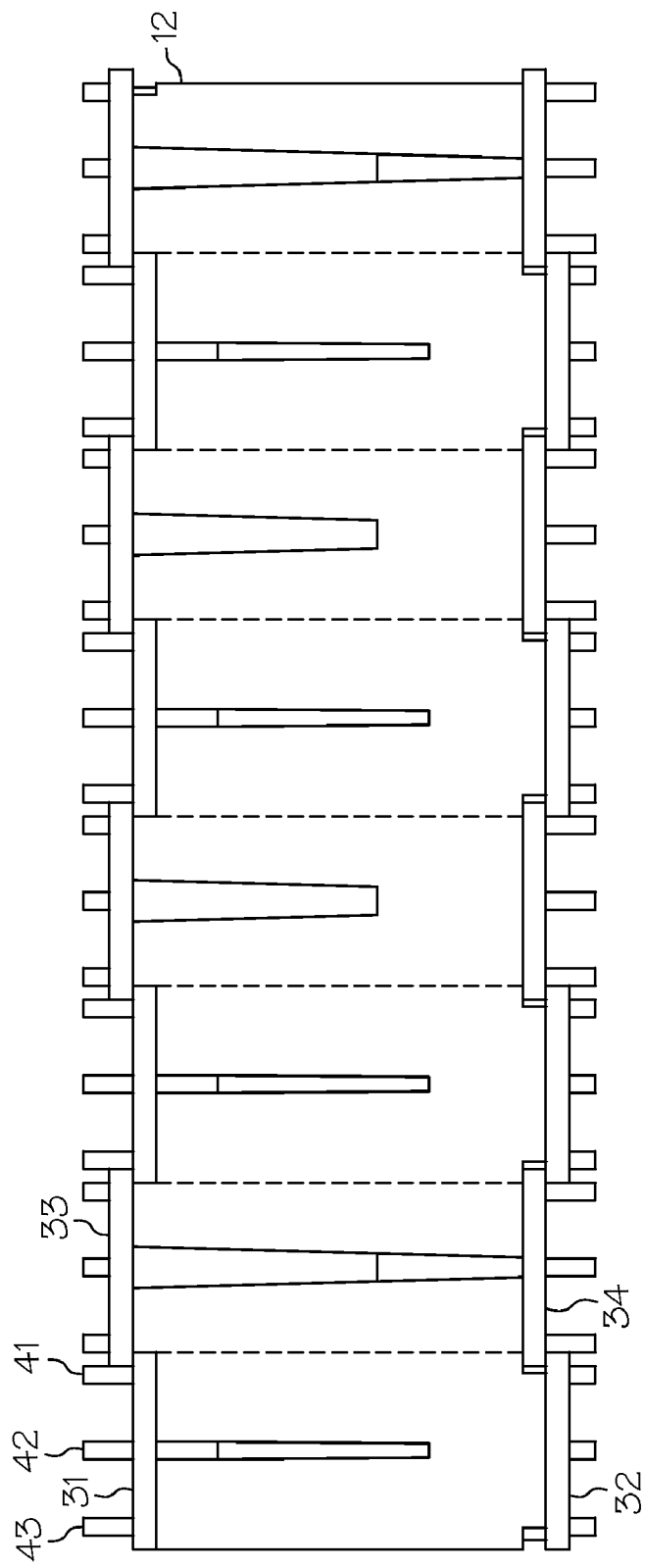
FIG. 4 shows a front view of the sample tube holder 11 in FIG. 1 in the direction of arrow 18 in FIG. 1.

FIG. 4 shows a front view of sample tube holder 11 in FIG. 1 in the direction of arrow 18 in FIG. 1. FIG. 4 shows that the garter springs 31, 33, and respectively 32, 34, of adjacent chambers 13 are not located at the same heights, but are located at heights which are offset with respect to each other. This feature allows a more compact arrangement of the chambers of the sample tube holder 11. The arrangement of the garter springs 31 and 33, and respectively 32, 34 shown in FIG. 1, also contributes to arrange chambers 13 close to each other and thereby achieve a compact arrangement of the chambers of the sample tube holder 11.

Figure 9:
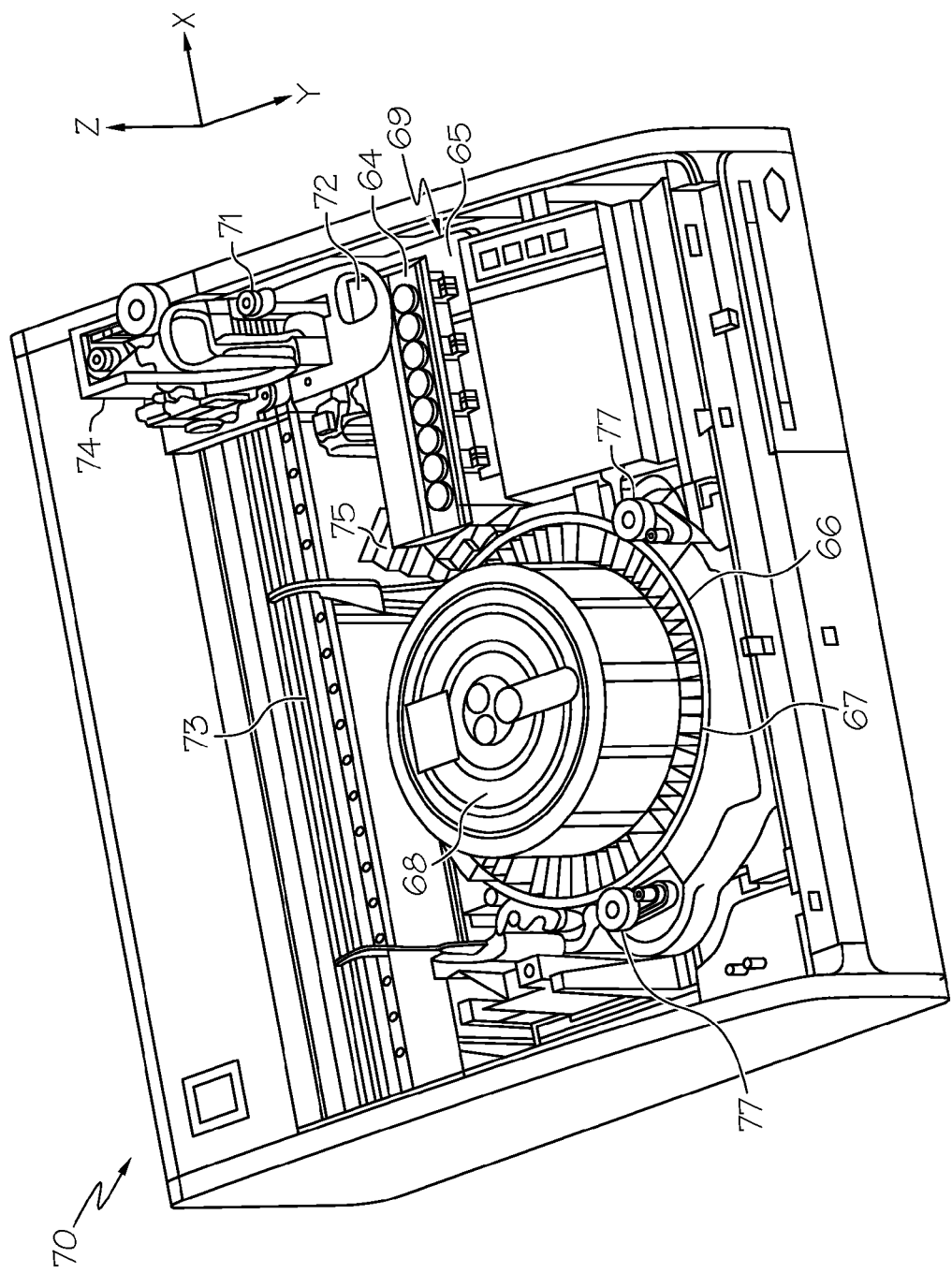
FIG. 9 shows a perspective view of a clinical chemistry analyzer comprising a sample tube holder according to the present invention.

FIG. 5 shows an exploded perspective view of the above described sample tube holder 11 and of components used for installing it in a clinical chemistry analyzer, such as analyzer 70 shown in FIG. 9. FIG. 5 shows a frame 61 for receiving solid body 12 of sample tube holder 11. Frame 61 is inserted into and connected to a suitable cavity of the analyzer 70, such as a sample tube area 69 shown by FIG. 9. FIG. 5 also shows a cover 62 with openings 63 which spatially correspond to the upper openings 15 of the chambers 13 of solid body 12. Cover 62 accurately fits into a corresponding opening of a cover plate (not shown) of the analyzer 70.

Figure 6:
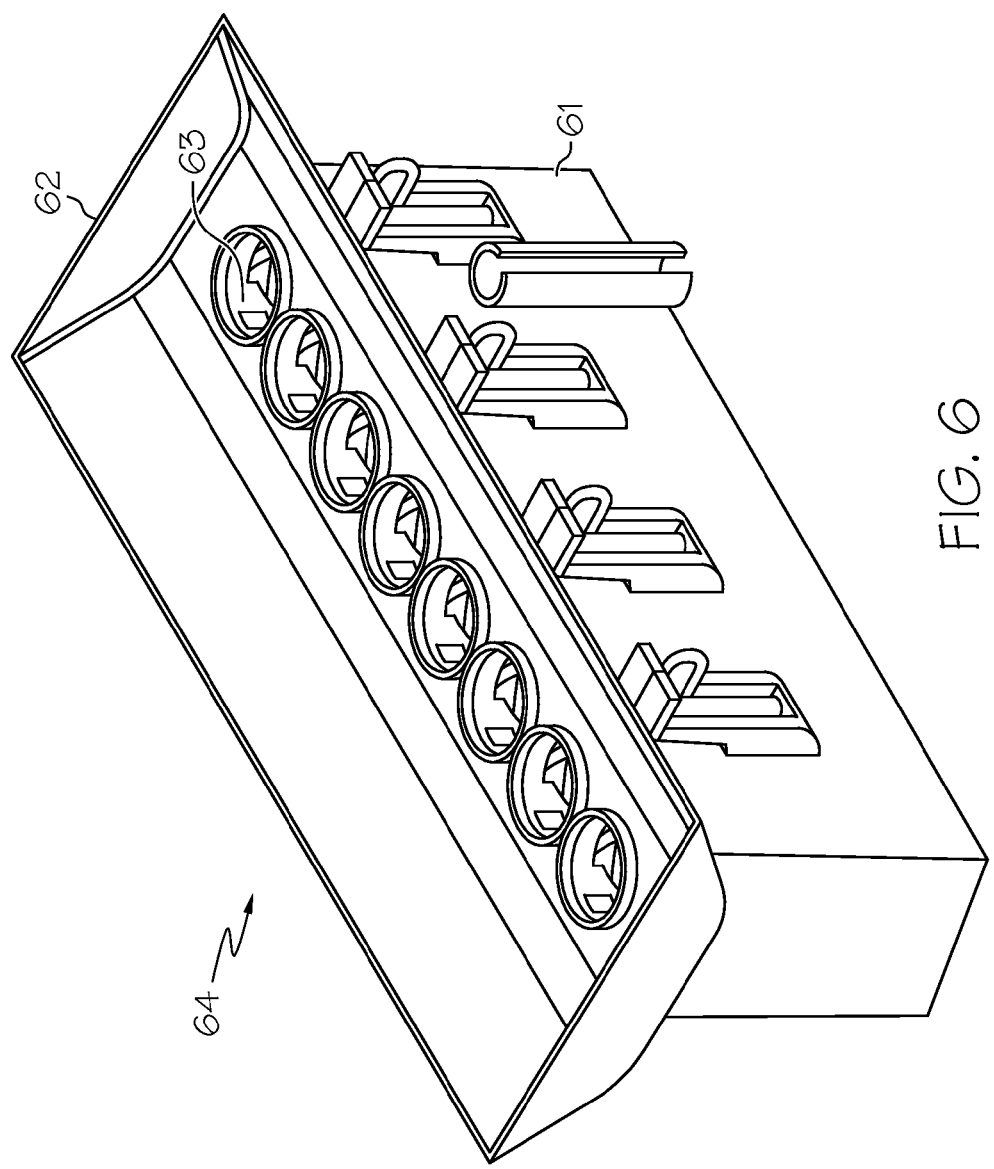
FIG. 6 shows a sample tube holder assembly 64 of the components shown by FIG. 5.

FIG. 6 shows a sample tube holder assembly 64 of the components shown by FIG. 5.

Figure 7:
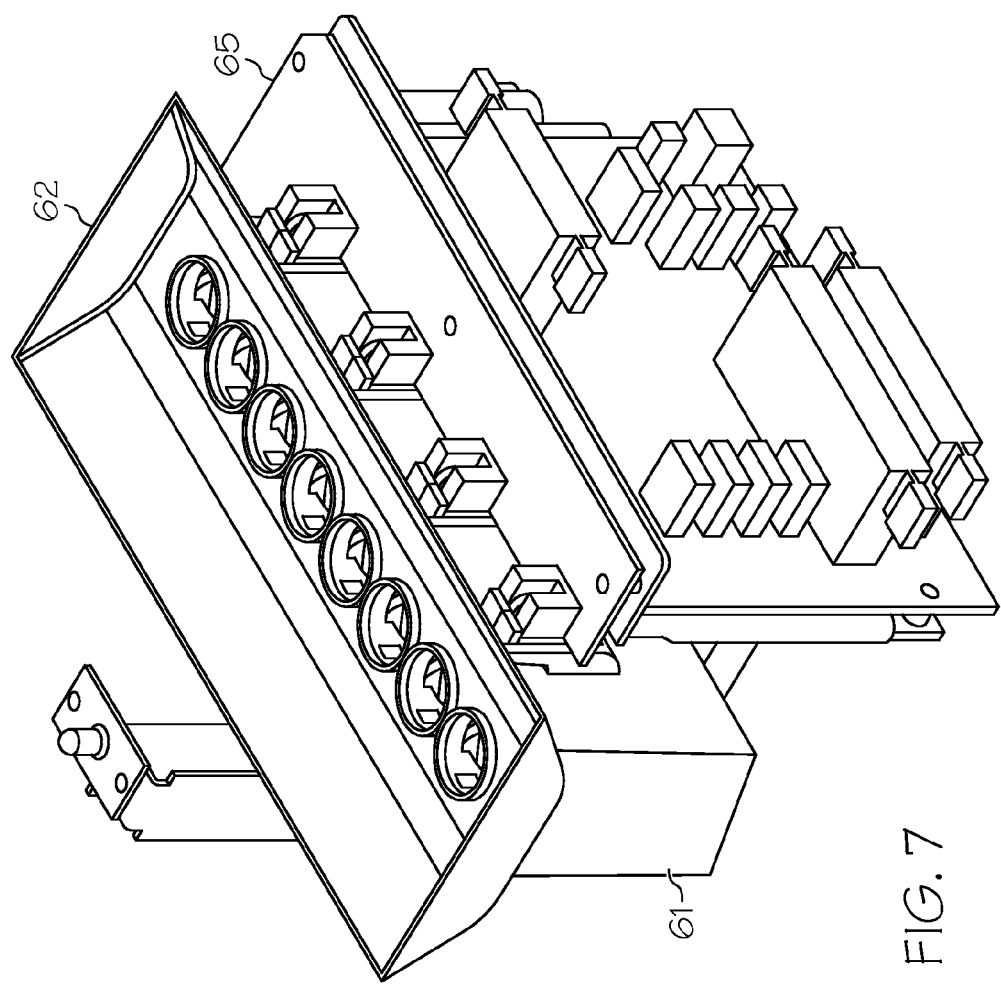
FIG. 7 shows the sample tube holder assembly 64 of FIG. 6 after is installed in a supporting frame 65.

FIG. 7 shows the assembly 64 of FIG. 6 after it is installed in a supporting frame 65 which is part of the analyzer 70.

Figure 8:
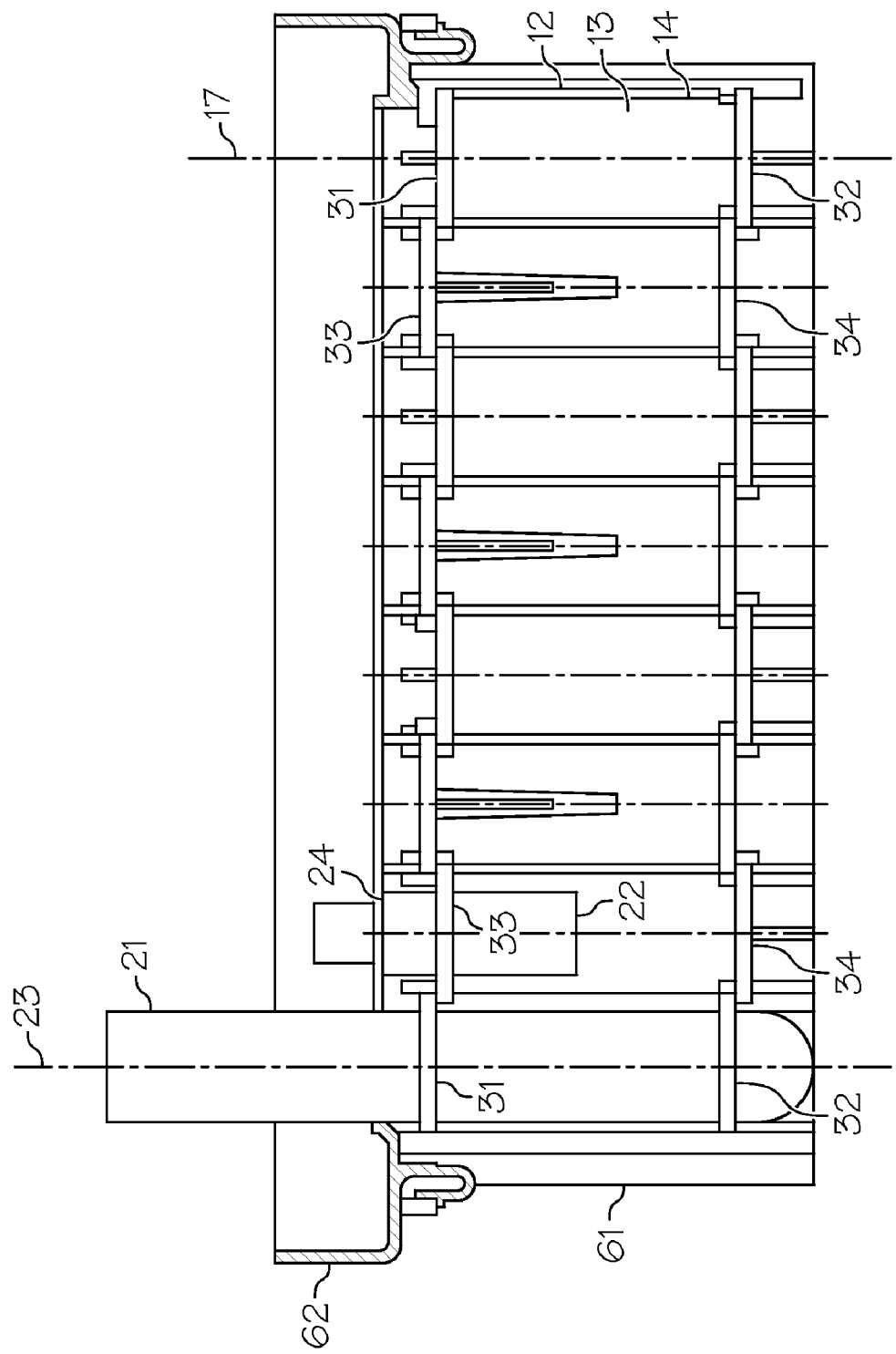
FIG. 8 shows a cross-sectional view of a sample tube holder assembly 64 in FIG. 6 and of sample tubes 21 and 22 inserted in respective chambers 13 of the sample tube holder 11 along a plane passing through a length symmetry axis of all chambers 13 of the sample tube holder 11.

FIG. 8 shows a cross-sectional view of the sample tube holder assembly 64 in FIG. 6 and of sample tubes 21 and 22 inserted in respective chambers 13 of sample tube holder 11 along a plane passing through the length symmetry axis 17 of all chambers 13 of sample tube holder 11. FIG. 8 shows the length symmetry axis 17 of one of chambers 13 of sample tube holder 11 and the length symmetry axis 23 of one of sample tubes 21, a longitudinal portion of which is inserted in one of the chambers 13 of sample tube holder 11.

In FIG. 8, a longitudinal portion of the first sample tube 21 having a first diameter is inserted in a first chamber 13 of sample tube holder 11 and sample tube 21 is centered and held in place in chamber 13 by garter springs 31 and 32.

In FIG. 8, a longitudinal portion of a second sample tube 22 having a second diameter smaller than the diameter of sample tube 21 is inserted in a second chamber 13 of sample tube holder 11. Sample tube 22 is shorter than sample tube 21 and also shorter than the length of chamber 13. The upper part of sample tube 22 has an annular flange 24 which fits on the upper rim of an opening 63 (see FIG. 5) of cover 62 when the lower portion of sample tube 22 is inserted into a chamber 13. Sample tube 22 is centered and held in place in second chamber 13 on the one hand by the fitting of flange 24 on the upper rim of opening 63 and on the other hand by garter spring 33 which holds the central part of sample tube 22.

As can be appreciated from FIG. 8, when a sample tube 21 respectively 22 is arranged in a chamber 13 there is a gap between the sample tube 21, 22 and the side walls 14 of the chamber 13. When sample tubes 21, 22 are arranged as shown by FIG. 8, each of garter springs 31, 32, 33, 34 is in direct contact with at least three points of the outer surface of sample tube 21 (respectively 22), and each of garter springs 31, 32, 33, 34 thereby holds a sample tube 21 (respectively 22) and brings the length symmetry axis 23 of the sample tube into coincidence with the length symmetry axis 17 of the corresponding chamber 13.

FIG. 9 shows a perspective view of the analyzer 70 comprising a sample tube holder assembly 64 according to the present invention. In one embodiment, the analyzer 70 is a clinical-chemistry analyzer for analyzing sample-reagent mixtures formed by mixing aliquots of biological samples taken from primary sample tubes and reagents contained in reagent containers. A sample tube holder 11 (FIG. 1) according to the invention is part of the sample tube holder assembly 64 and is installed in the sample tube area 69 located adjacent to a conveyor 66 for conveying reaction cuvettes 67 inserted in corresponding cavities of conveyor 66 along a circular path. A removable reagent container assembly 68 containing a plurality of reagent containers is installed in the central part of conveyor 66. The analyzer 70 shown by FIG. 9 further comprises an automatic pipetting unit 71, a photometer 75 located adjacent to the conveyor 66, and conveyor driving means 77 for rotating conveyor 66.

Automatic pipetting unit 71 is suitable for effecting all pipetting operations in the analyzer 70, e.g. the pipetting of a sample portion taken from a sample tube held by the sample tube holder assembly 64 in the sample area 69 into a reaction cuvette 67 in conveyor 66 and the pipetting of a reagent volume taken from a reagent container in reagent container assembly 68 into a reaction cuvette 67 in conveyor 66. After these pipetting operations, the reaction cuvette 67 contains a sample-reagent-mixture.

Figure 10:
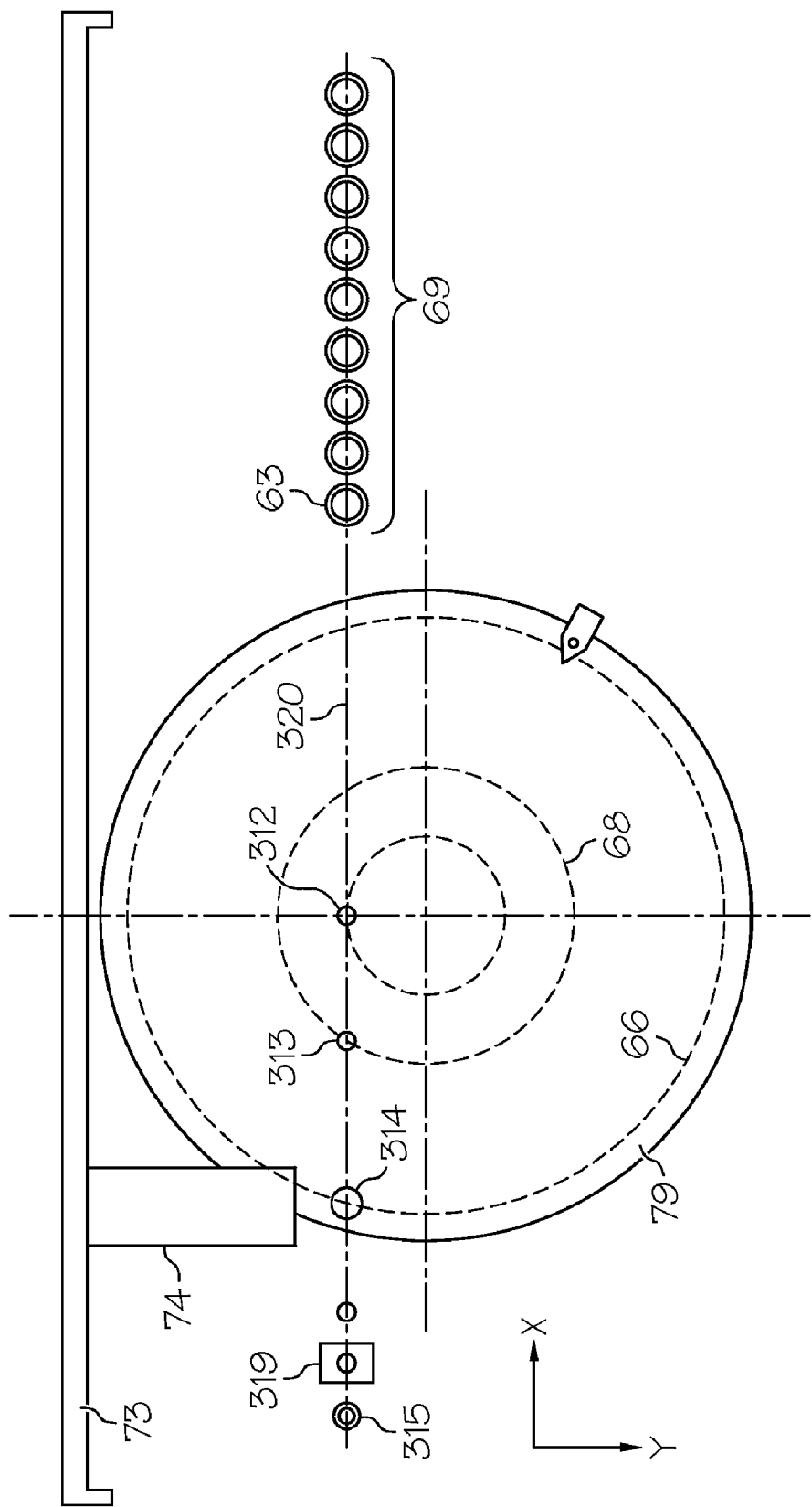
FIG. 10 shows a schematic top view of the analyzer shown by FIG. 9 and in particular the arrangement of pipetting openings in a cover of the analyzer.

Automatic pipetting unit 71 comprises a removably mounted pipetting needle 72 and a transport device 74 mounted on a rail 73 which extends in the X-direction shown in FIGS. 9 and 10. This transport device 74 moves the pipetting needle 72 along a rectilinear path in the X-direction for bringing pipetting needle 72 to several pipetting positions, in a particular a pipetting position in the sample tube area 69 for taking an aliquot of a sample to be analyzed, another pipetting position for taking an aliquot of a reagent from a reagent container and another pipetting position for delivering the sample and reagent aliquots into a reaction cuvette 67 installed in the conveyor 66.

In one embodiment, the transport device 74 is a needle transport head which is moved along the rail 73 in FIG. 9 for moving pipetting needle 72 along a straight line in a first direction, e.g. in a direction parallel to the X-axis in FIG. 1, to a plurality of pipetting positions all of which have centers that lie in one and the same vertical plane, e.g. a plane which is parallel to the X-Z-plane min FIG. 1, and which passes through the above mentioned straight line.

The location of the above-mentioned pipetting positions is illustrated by FIG. 10 which shows a schematic top plan view of the analyzer 70 of FIG. 9. FIG. 10 shows a top plan view of a cover 79 of the analyzer 70 shown by FIG. 9. The cover 79 has the following openings which allow performing pipetting operations with pipetting needle 72: a first opening 312 for taking a reagent volume from a reagent container (not shown) provided in the reagent container assembly 68, a second opening 313 for taking a reagent volume from another reagent container (not shown) provided in the reagent container assembly 68, a third opening 314 for performing pipetting operations in one of the reaction cuvettes 67 on conveyor 66, a fourth opening 319 for contacting a reference member for performing an initialization method and for accessing washing station and a fifth opening 315 for performing pipetting operations in a chamber of an ISE device.

The centers of the above mentioned openings in the cover 79 of the analyzer 70 shown by FIG. 9 define the location of pipetting positions to which pipetting needle 72 has to be brought to by transport head 74.

FIG. 10 also shows, on the right side, the sample area 69 and the upper openings 63 of the cover of the sample tube holder assembly 64 which holds sample tubes. The centers of the openings 63 are further pipetting positions to which pipetting needle 72 is brought to by transport head 74.

As shown by FIGS. 9 and 10, all above-mentioned pipetting positions have centers which lie in one and the same vertical plane, which is parallel to the X-Z-plane and which passes through the straight line in X-direction along which pipetting needle 72 is moved by transport head 74. In FIG. 10, the plane where all the centers of the pipetting positions lie is represented by straight line which is called pipetting axis 320 for the purpose of this description.

Another illustrative embodiment of a sample tube holder according to the present invention is described hereinafter with reference to FIGS. 11 to 20.

Figure 11:
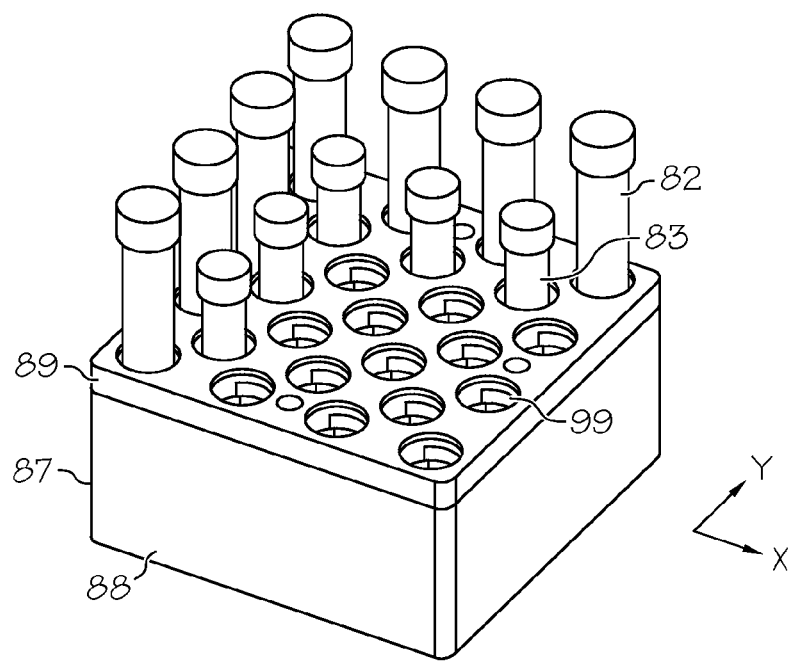
FIG. 11 shows a perspective view of another embodiment sample tube holder according to the present invention with sample tubes inserted in chambers of the holder.

FIG. 11 shows a sample tube holder 81 for receiving and holding a plurality of sample tubes 82, 83 having a cylindrical shape and outer diameters, in one embodiment, lying in a predetermined range, e.g. from about 7 millimeters to about 17 millimeters.

Figure 16:
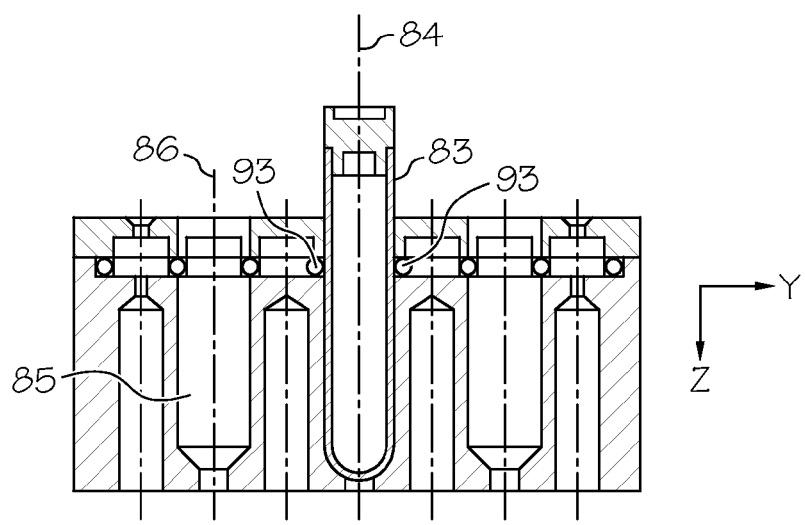
FIG. 16 shows a cross-sectional view of sample tube holder 81 and of a sample tube 82 along a plane A-A in FIG. 15.
Figure 19:
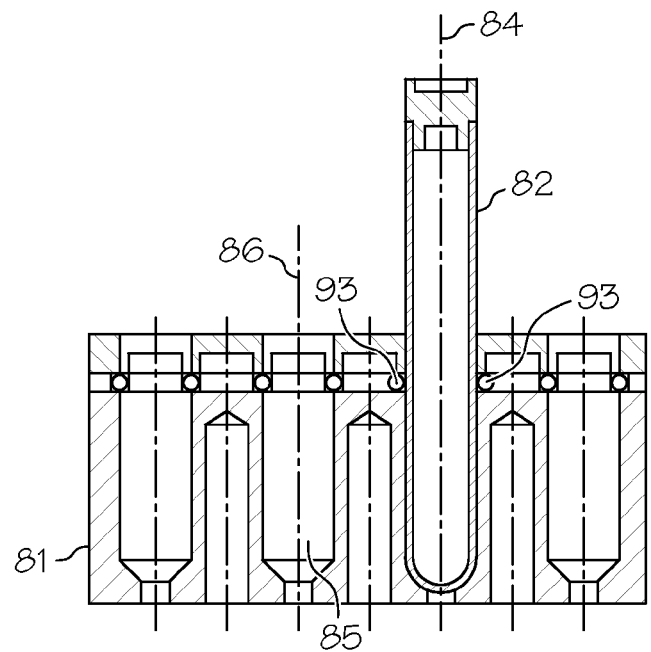
FIG. 19 shows a cross-sectional view of sample tube holder 81 and of a sample tube 82 along a plane B-B in FIG. 17.
Figure 20:
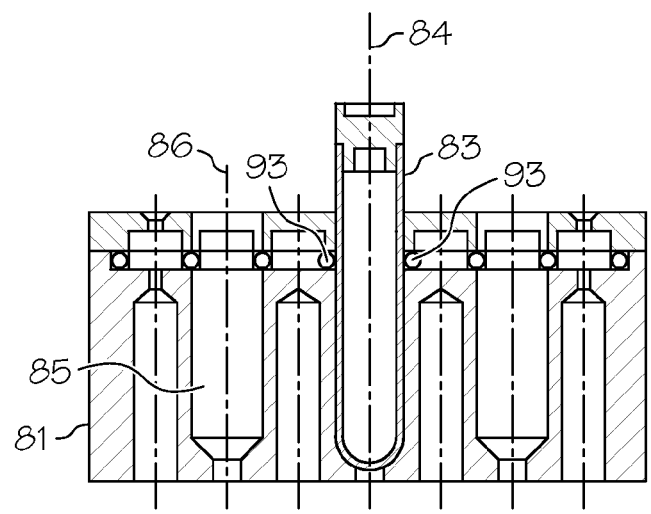
FIG. 20 shows a cross-sectional view of sample tube holder 81 and of a sample tube 83 along a plane C-C in FIG. 17.

As shown by FIGS. 16, 19 and 20, each sample tube 82, 83 has a longitudinal symmetry axis 84.

In one embodiment, shown in particular by FIGS. 11 to 14, sample tube holder 81 comprises a housing 87, which comprises a housing base 88 and a housing cover 89.

The matrix array of chambers described hereinafter and the grid structure associated therewith can however be built as a self-supporting structure, i.e. without any housing around them.

Figure 15:
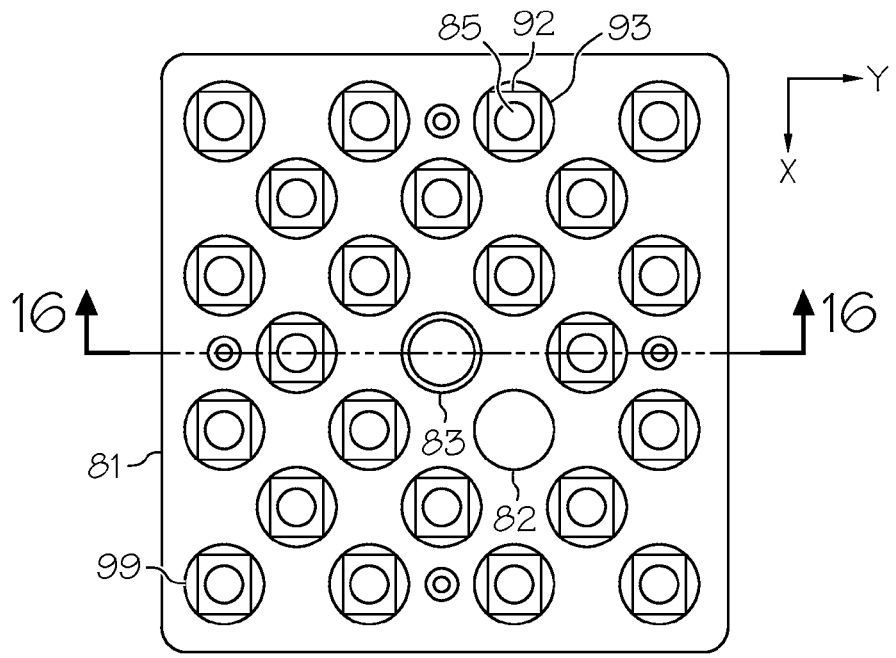
FIG. 15 shows a top view of the sample tube holder shown in FIG. 11 including the housing cover 89 and a sample tube 82 inserted in a chamber located in the central portion of sample tube holder 81.

As shown by FIGS. 15 and 16, sample tube holder 81 comprises a matrix array of elongated chambers 85. Each of these chambers is adapted for receiving at least a portion of a sample tube 82, 83. Each of chambers 85 has a longitudinal symmetry axis 86 and a cross-section which is larger than the largest cross-section of a sample tube 82, 83 to be inserted in one of chambers 85.

Figure 12:
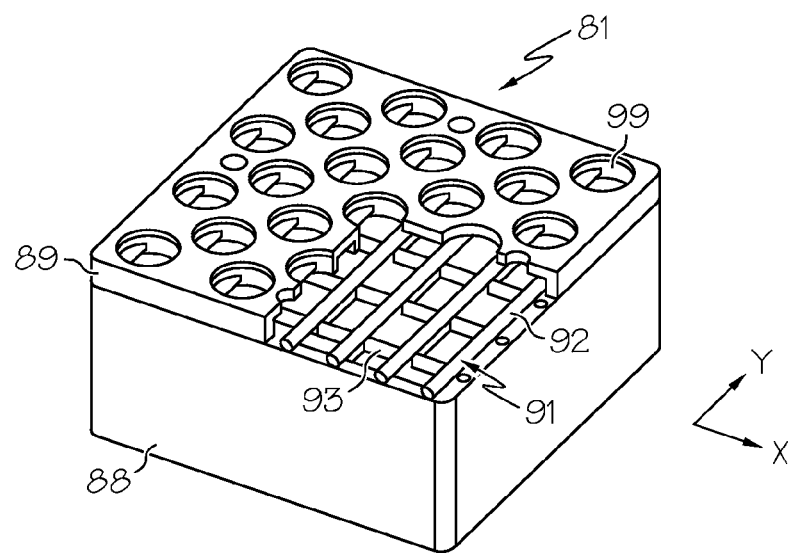
FIG. 12 shows a perspective view of the sample tube holder shown in FIG. 11.
Figure 13:
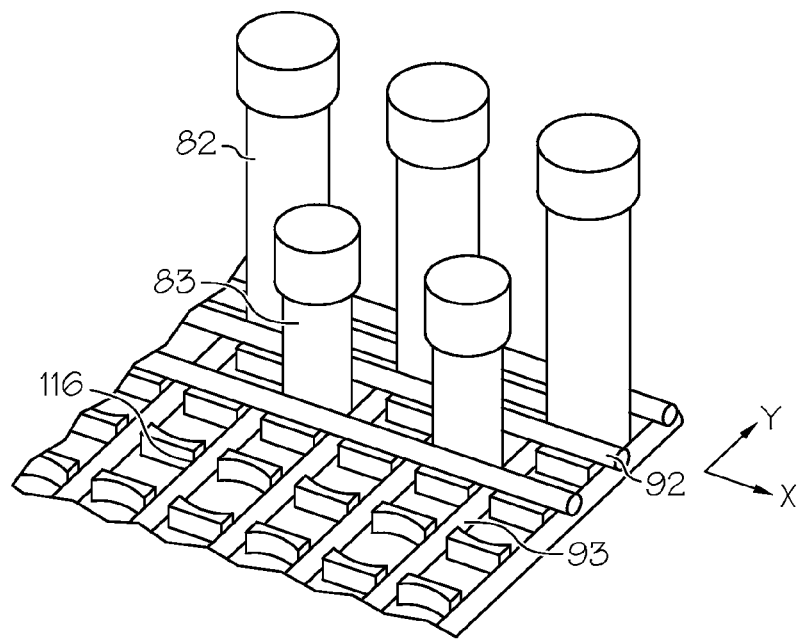
FIG. 13 shows a schematic enlarged perspective view of a portion of the sample tube holder shown in FIG. 11 and sample tubes positioned in that holder.

As shown by FIGS. 12 and 13, sample tube holder 81 further comprises a grid structure 91 formed by the superposition of a first array of elongated elastic elements 92, which extend in a first direction Y, and of a second array of elongated elastic elements 93, which extend in a second direction X, and which in one embodiment is perpendicular to said first direction Y. In other embodiments, the X direction can however form with the Y direction, an angle which differs from an angle of 90 degrees. Each of elastic elements 92, 93 has a longitudinal symmetry axis. The longitudinal symmetry axis of the elastic elements 92 of the first array lies in a first plane and the longitudinal symmetry axis of the elastic elements 93 of the second array lies in a second plane which is parallel to the first plane.

The axis X and Y represented in the accompanying drawings define a horizontal plane. As shown by FIG. 16, the longitudinal symmetry axis 86 of each chamber 85 and the longitudinal symmetry axis 84 of a sample tube arranged in such a chamber are perpendicular to that plane.

Figure 17:
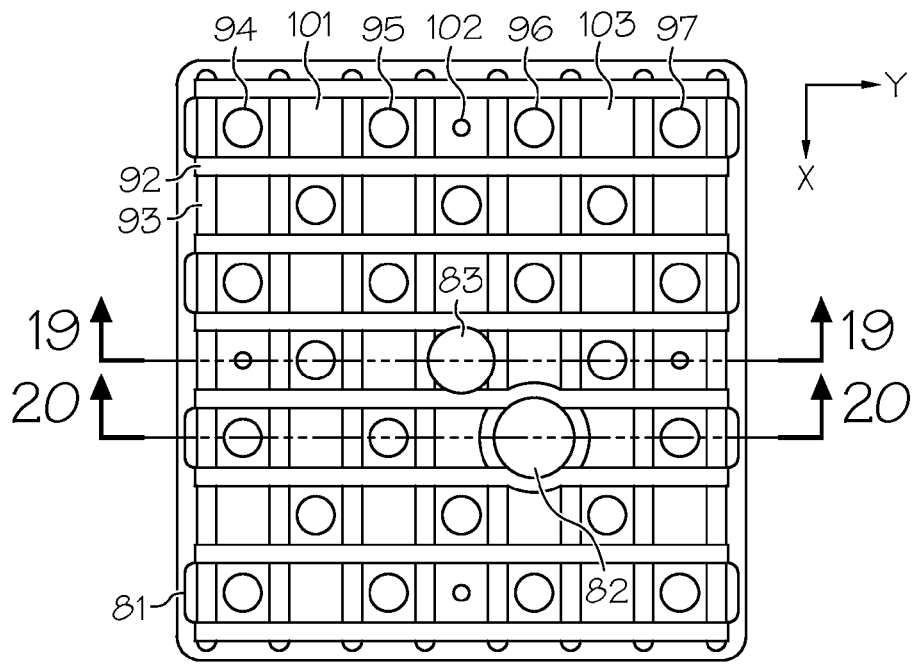
FIG. 17 shows a top view of the sample tube holder 81 shown in FIG. 11 without housing cover 89, with sample tubes 82 and 83 inserted in respective openings of a grid structure 91 formed by the superposition of a first array of elongated elastic elements 92, which extend in Y-direction, and of a second array of elongated elastic elements 93, which extend in a X-direction that is perpendicular to the X-direction.

In one embodiment as shown by FIGS. 12 and 17, the elastic elements 92 of the first array are uniformly spaced in the second direction X and the elastic elements 93 of said second array are uniformly spaced in said first direction Y, and the spacing between neighboring elements is the same in both directions.

Figure 18:
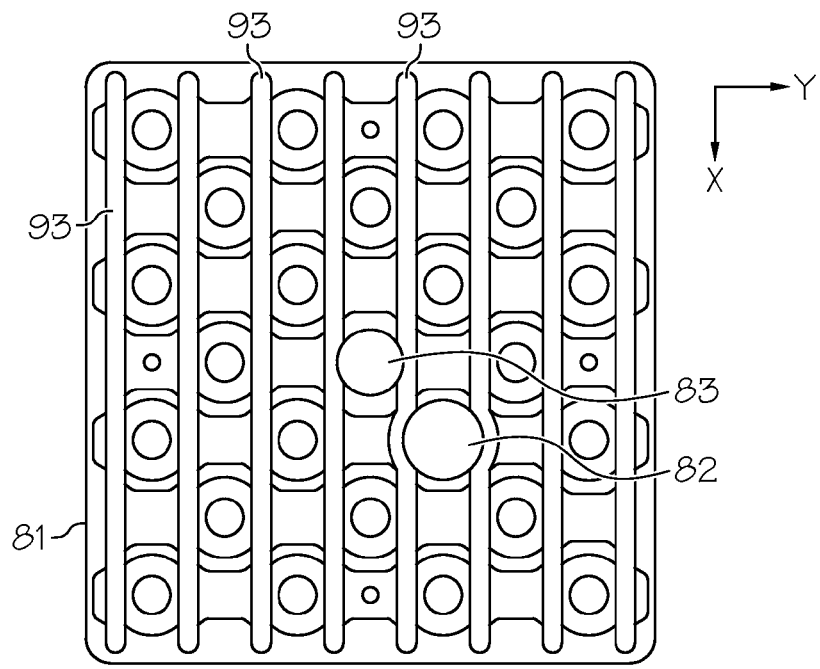
FIG. 18 shows a top view of the sample tube holder 81 similar to FIG. 17 without housing cover 89 and without the first array of elongated elastic elements 92 which extend in the first direction Y.

FIG. 17 shows a top view of the sample tube holder 81 shown in FIG. 11 without the housing cover 89, with sample tubes 82 and 83 inserted in respective openings of a grid structure 91 formed by the superposition of a first array of elongated elastic elements 92, which extend in Y-direction, and of a second array of elongated elastic elements 93, which extend in a X-direction which is perpendicular to the X-direction. FIG. 18 shows a top view of the sample tube holder 81 similar to FIG. 17 without the housing cover 89 and without the first array of elongated elastic elements 92 which extend in the first direction Y. FIGS. 17 and 18 show the deformations of elastic elements 92 and 93 caused by the insertion of sample tubes 82 and 83.

FIG. 19 shows a cross-sectional view of sample tube holder 81 and of a sample tube 82 along a plane B-B in FIG. 17.

FIG. 20 shows a cross-sectional view of sample tube holder 81 and of a sample tube 83 along a plane C-C in FIG. 17.

As shown by FIG. 17, grid structure 91 has openings formed by segments of elastic elements 92 of said first set of elastics elements and segments of said second set of elastics elements 93. In FIG. 17, openings 94 to 97 and 101 to 103 are in the first row of openings of grid structure 91. All openings of grid structure 91 are smaller than the smallest cross-section of a sample tube 82, 83 to be inserted in one of chambers 85. In the embodiment shown by FIG. 17, each of the openings of grid structure 91 is square shaped. In other embodiments, wherein the X and Y directions form an angle which differs from 90 degrees, the openings of grid structure 91 can have the shape of a parallelogram, and in still other embodiments, the shape of a rhombus.

Grid structure 91 is so operatively associated with the matrix array of chambers 85 that when a sample tube 82, 83 is inserted through one of the openings of grid structure 91, the longitudinal symmetry axis 84 of the sample tube 82 or 83 coincides with the longitudinal symmetry axis 86 of the corresponding chamber 85. For this purpose each of chambers 85 of array of chambers is aligned with one of the openings of grid structure 91.

In FIG. 17, each of the openings which are aligned with corresponding chambers 85 of the matrix array of chambers is recognizable by a circle in the center of the opening. That circle corresponds to the bottom of a chamber 85 aligned with that opening. As can be appreciated from FIG. 17, not every one of openings in the first row of openings of grid structure 91 is aligned with a chamber 85. For instance of the first row of openings represented in FIG. 17 in Y-direction, openings 94 to 97 are each aligned with a chamber and openings 101 to 103 are not. This also applies to rows of openings in X-direction. Therefore, of adjacent openings in the same row only one of them is aligned with a chamber. The distribution of openings which are aligned with corresponding chambers is thus as shown by FIG. 17, i.e. four of them in the first row, three of them in the second row, four of them in the third row and so on.

In one embodiment shown by FIGS. 11 to 14, the above described matrix array of chambers 85 and the grid structure 91 snuggly fit in housing 87.

In another embodiment shown by FIGS. 11, 12 and 15, 16, housing cover 89 has a matrix array of openings 99 each of which is aligned with one of the openings of grid structure 91 and with one of the chambers 85 of the matrix array of chambers. In order to accurately center a sample tube in one of the chambers of sample tube holder 81, the user of this holder introduces a sample tube of any size through one of openings 99 and through the grid opening aligned therewith and thereby accurately centers the sample tube in the chamber which is aligned with both the grid opening and the corresponding opening 99 of housing cover 89.

FIG. 15 shows a top view of the sample tube holder shown in FIG. 11 including the housing cover 89, a sample tube 83 inserted in a chamber located in the central portion of sample tube holder 81 and a sample tube 82 inserted in another chamber. FIG. 16 shows a cross-sectional view of sample tube holder 81 and of a sample tube 83 along a plane A-A in FIG. 15. As shown by FIG. 16, elastic elements 93 contribute to position sample tube 83 in a centered position in a chamber 85 of sample tube holder. In the illustrated embodiment, the conical bottom surface of chamber 85 contributes to put sample tube 83 in vertical position. In FIG. 16, the vertical direction is indicated by a Z-axis perpendicular to the plane defined by the X- and Y-axis.

Figure 14:
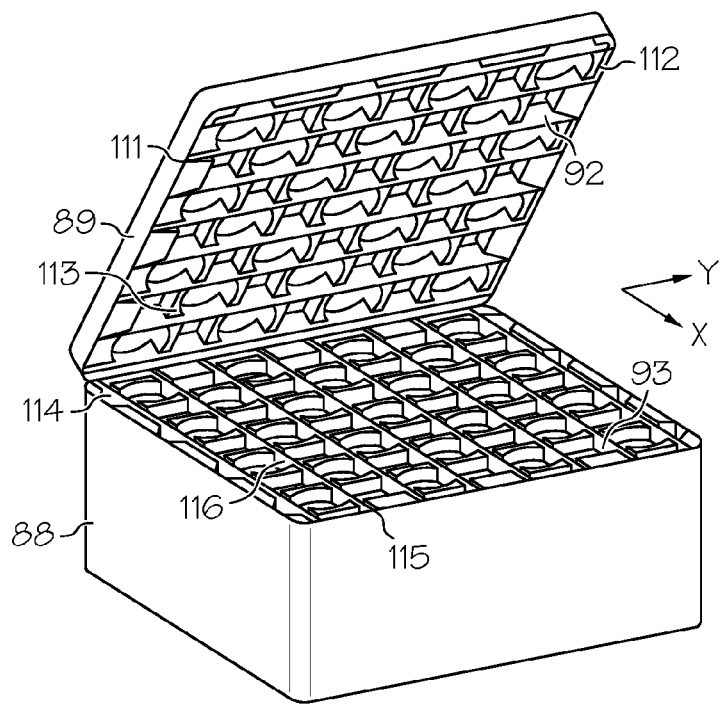
FIG. 14 shows a perspective view of the sample tube holder shown in FIG. 12 with the housing cover 89 separated from the housing base 88.

In one embodiment shown by FIG. 14, guide elements 111, 112, 113, 114, 115, 116 which limit the freedom of movement of each of the elastic elements which form grid structure 91 are arranged within housing cover 89 and in the upper portion of housing base 88.

For this purpose, housing cover 89 comprises guide elements 111, 112 of a first type located at opposite ends of each elastic element 92. These guide elements 111, 112 prevent motion of each elastic element along its longitudinal symmetry axis, i.e. in Y-direction. In one embodiment, the guide elements 111, 112 of the first type just mentioned are portions of side walls of housing cover 89. Housing cover 89 further comprises guide elements 113 of a second type arranged in housing cover 89 and located at uniformly spaced points along each of the elastic elements 92. These guide elements 113 prevent motion of those points of each elastic element 92 in a direction normal to the longitudinal axis of the elastic element 92, i.e. motion in X-direction. Each of latter uniformly spaced points is aligned with one of the corners of one of the openings of grid structure 91.

In a similar way, housing base 88 comprises guide elements 114, 115 of a first type located at opposite ends of each elastic element 93. These guide elements 114, 115 prevent motion of each elastic element 93 along its longitudinal symmetry axis, i.e. in X-direction. The guide elements 114, 115 of the first type in one embodiment are portions of side walls of housing base 88. Housing base 88 further comprises guide elements 116 of a second type arranged in housing base 88 and located at uniformly spaced points along each of the elastic elements 93. These guide elements 116 prevent motion of those points of each elastic element 93 in a direction normal to the longitudinal axis of the elastic element 93, i.e. motion in Y-direction. Each of latter uniformly spaced points is aligned with one of the corners of one of the openings of grid structure 91.

In one embodiment shown by FIGS. 13 and 14, each of the chambers 85 of the matrix array of chambers has side walls which have each an upper end edge, and each of the guide elements 116 of the second type in housing base 88 is a U-shaped notch in one of said upper end edges. The guide elements 111, 112 of the second type in housing cover 89 may have the same or a similar structure as the guide elements 116 of the second type in housing base 88.

In one embodiment, each of the opposite ends of each elastic element 92, 93 is not connected to a fixed point, and the elastic elements 92, 93 are not under any pre-stressing. In this illustrative embodiment, each of the elastic elements 92, 93 is a worm-shaped helical spring or a compression spring.

In another embodiment, each of the opposite ends of each elastic element 92, 93 is connected to a fixed point and each of the elastic elements is under a predetermined pre-stressing. In this illustrative embodiment, each of the elastic elements 92, 93 is a tension spring or a worm-shaped helical spring.

Although various embodiments of the invention have been described using specific terms, such description is for illustrative purposes only, and it is to be understood that changes and variations obvious to the skilled artisan are to be considered within the scope and spirit of the subject application, which is only to be limited by the claims that follow and their equivalents.

What is claimed is:

1. A sample tube holder for receiving and holding a sample tube having a cylindrical shape, a length symmetry axis and an outer diameter lying in a predetermined range, said sample tube holder comprising:
   a solid body comprising at least one elongated chamber having side walls, a first opening in a top of the solid body, and a length symmetry axis, said chamber being adapted for receiving a longitudinal portion of a sample tube through said opening;
   a first array of pins extending upwardly from said solid body and a plane formed by said first opening, said first array of pins comprising rigid longitudinal projections of the side walls of said chamber extending away from said first opening; and
   an elastic element stretched around said first array of pins, wherein when a sample tube is arranged in said chamber there is a gap between the sample tube and the side walls of the chamber, and the elastic element is in direct contact with at least three points of an outer surface of said sample tube, the elastic element thereby holding said sample tube and bringing the length symmetry axis of said sample tube into coincidence with the length symmetry axis of said chamber,
   wherein said solid body comprises a second opening opposed to said first opening, and a second array of pins which are rigid longitudinal projections of the side walls of said chamber and extend away from said second opening, and
   wherein a second elastic element is stretched around said second array of pins.

2. A sample tube holder according to claim 1, wherein said solid body is made of a plastic material.

3. A sample tube holder according to claim 1, wherein each said elastic element is a garter spring made of stainless steel and has a body having a width lying in a range from about 1.5 to about 2.0 millimeters.

4. A sample tube holder according to claim 1, wherein the center of each of said pins of said second array of pins is located at the corners of a regular polygon.

5. A sample tube holder according to claim 4, wherein said corners lie on a first circle in a plane normal to the length symmetry axis of said chamber, the center of said first circle lying on the length symmetry axis of said chamber, said first circle having a surface which is larger than the cross-section of said chamber.

6. A sample tube holder according to claim 1, wherein the center of each of said pins is located at the corners of a regular polygon, wherein said corners lie on a first circle in a plane normal to the length symmetry axis of said chamber, the center of said first circle lying on said the length symmetry axis of said chamber, said first circle having a surface which is larger than the cross-section of said chamber, and wherein said elastic element in a resting state extends along a second circle having a diameter which is smaller than the diameter of said first circle.

7. A sample tube holder according to claim 4, wherein said regular polygon is an equilateral triangle.

8. A sample tube holder according to claim 1, wherein the diameter of a circle inscribed in a regular polygon defined by inner sides of said elastic element is smaller than 11 millimeters.

9. A sample tube holder according to claim 1, wherein said chamber is adapted for receiving a sample tube having an outer diameter lying in a range from about 7 to about 17 millimeters.

10. A sample tube holder according to claim 9, wherein a diameter of a circle inscribed in a regular polygon defined by inner sides of said elastic element is smaller than 7 millimeters.

11. A sample tube holder according to claim 1, wherein said at least one elongated chamber is a plurality of such chambers having each the same shape and dimensions and provided in a rectilinear array, and said sample tube holder is thereby adapted for receiving and holding a plurality of sample tubes.

12. A sample tube holder for receiving and holding a sample tube having a cylindrical shape, a length symmetry axis and an outer diameter lying in a predetermined range, said sample tube holder comprising:
   a solid body comprising at least one elongated chamber having side walls, a first opening, a second opening opposed to said first opening, and a length symmetry axis, said chamber being adapted for receiving a longitudinal portion of a sample tube through said opening;
   a first array of pins which are rigid longitudinal projections of the side walls of said chamber extending away from said first opening;
   a second array of pins which are rigid longitudinal projections of the side walls of said chamber and extend away from said second opening,
   a first elastic element stretched around said first array of pins; and
   a second elastic element is stretched around said second array of pins;
   wherein when a sample tube is arranged in said chamber there is a gap between the sample tube and the side walls of the chamber, and the first elastic element is in direct contact with at least three points of an outer surface of said sample tube, the first elastic element thereby holding said sample tube and bringing the length symmetry axis of said sample tube into coincidence with the length symmetry axis of said chamber.

13. A sample tube holder according to claim 12, wherein said solid body is made of a plastic material.

14. A sample tube holder according to claim 12, wherein each said elastic element is a garter spring made of stainless steel and has a body having a width lying in a range from about 1.5 to about 2.0 millimeters.

15. A sample tube holder according to claim 12, wherein the center of each of said pins of said first array of pins is located at the corners of a regular polygon.

16. A sample tube holder according to claim 12, wherein the center of each of said pins of said second array of pins is located at the corners of a regular polygon.

17. A sample tube holder according to claim 15, wherein said corners lie on a first circle in a plane normal to the length symmetry axis of said chamber, the center of said first circle lying on the length symmetry axis of said chamber, said first circle having a surface which is larger than the cross-section of said chamber.

18. A sample tube holder according to claim 12, wherein the center of each of said pins in said first and second arrays is located at the corners of a regular polygon, wherein said corners lie on a first circle in a plane normal to the length symmetry axis of said chamber, the center of said first circle lying on said the length symmetry axis of said chamber, said first circle having a surface which is larger than the cross-section of said chamber, and wherein said elastic element in a resting state extends along a second circle having a diameter which is smaller than the diameter of said first circle.

19. A sample tube holder according to claim 15, wherein said regular polygon is an equilateral triangle.

20. A sample tube holder according to claim 12, wherein the diameter of a circle inscribed in a regular polygon defined by inner sides of said elastic element is smaller than 11 millimeters.

21. A sample tube holder according to claim 12, wherein said chamber is adapted for receiving a sample tube having an outer diameter lying in a range from about 7 to about 17 millimeters.

22. A sample tube holder according to claim 21, wherein a diameter of a circle inscribed in a regular polygon defined by inner sides of said elastic element is smaller than 7 millimeters.

23. A sample tube holder according to claim 12, wherein said at least one elongated chamber is a plurality of such chambers having each the same shape and dimensions and provided in a rectilinear array, and said sample tube holder is thereby adapted for receiving and holding a plurality of sample tubes.

24. A sample tube holder for receiving and holding a sample tube having a cylindrical shape, a length symmetry axis and an outer diameter lying in a predetermined range, said sample tube holder comprising:
   a solid body comprising at least one elongated chamber having side walls, a first opening in a top of the solid body, and a length symmetry axis, said chamber being adapted for receiving a longitudinal portion of a sample tube through said opening;
   a first array of pins extending upwardly from said solid body and a plane formed by said first opening, said first array of pins comprising rigid longitudinal projections of the side walls of said chamber extending away from said first opening, wherein the center of each of said pins of said first array of pins is located at the corners of a regular polygon; and
   an elastic element stretched around said first array of pins, wherein when a sample tube is arranged in said chamber there is a gap between the sample tube and the side walls of the chamber, and the elastic element is in direct contact with at least three points of an outer surface of said sample tube, the elastic element thereby holding said sample tube and bringing the length symmetry axis of said sample tube into coincidence with the length symmetry axis of said chamber,
   wherein said solid body further comprises a second opening opposed to said first opening, and a second array of pins which are rigid longitudinal projections of the side walls of said chamber and extend away from said second opening, and
   wherein a second elastic element is stretched around said second array of pins.

25. A sample tube holder according to claim 24, wherein said solid body is made of a plastic material.

26. A sample tube holder according to claim 24, wherein each said elastic element is a garter spring made of stainless steel and has a body having a width lying in a range from about 1.5 to about 2.0 millimeters.

27. A sample tube holder according to claim 24, wherein the center of each of said pins of said second array of pins is located at the corners of a regular polygon.

28. A sample tube holder according to claim 24, wherein said corners lie on a first circle in a plane normal to the length symmetry axis of said chamber, the center of said first circle lying on the length symmetry axis of said chamber, said first circle having a surface which is larger than the cross-section of said chamber.

29. A sample tube holder according to claim 24, wherein the center of each of said pins is located at the corners of a regular polygon, wherein said corners lie on a first circle in a plane normal to the length symmetry axis of said chamber, the center of said first circle lying on said the length symmetry axis of said chamber, said first circle having a surface which is larger than the cross-section of said chamber, and wherein said elastic element in a resting state extends along a second circle having a diameter which is smaller than the diameter of said first circle.

30. A sample tube holder according to claim 24, wherein said regular polygon is an equilateral triangle.

31. A sample tube holder according to claim 24, wherein the diameter of a circle inscribed in a regular polygon defined by inner sides of said elastic element is smaller than 11 millimeters.

32. A sample tube holder according to claim 24, wherein said chamber is adapted for receiving a sample tube having an outer diameter lying in a range from about 7 to about 17 millimeters.

33. A sample tube holder according to claim 32, wherein a diameter of a circle inscribed in a regular polygon defined by inner sides of said elastic element is smaller than 7 millimeters.

34. A sample tube holder according to claim 24, wherein said at least one elongated chamber is a plurality of such chambers having each the same shape and dimensions and provided in a rectilinear array, and said sample tube holder is thereby adapted for receiving and holding a plurality of sample tubes.

* * * * *

UNITED STATES PATENT AND TRADEMARK OFFICE
CERTIFICATE OF CORRECTION

| | | |
|---|---|---|
| PATENT NO. | : 8,147,777 B2 | Page 1 of 1 |
| APPLICATION NO. | : 11/643639 | |
| DATED | : April 3, 2012 | |
| INVENTOR(S) | : Gottlieb Schacher et al. | |

It is certified that error appears in the above-identified patent and that said Letters Patent is hereby corrected as shown below:

Col. 2, Line 56, "after is installed" should read --after it is installed--

Col. 5, Line 23, "to an suitably" should read --to a suitably--

Col. 6, Lines 57-58, "21 respectively 22" should read --21 (respectively 22)--

Col. 7, Line 27, "sample-reagent-mixture" should read --sample reagent mixture--

Col. 7, Lines 33-34, "in a particular" should read --in particular--

Col. 7, Line 45, "X-Z plane min" should read --X-Z-plane--

Col. 7, Line 46, "above mentioned" should read --above-mentioned--

Col. 7, Line 63, "above mentioned" should read --above-mentioned--

Col. 9, Lines 14-15, "of elastics elements" should read --of elastic elements--

Col. 9, Lines 15-16, "set of elastics elements" should read --set of elastic elements--

Col. 9, Line 40, "For instance of the" should read --For instance, in the--

Signed and Sealed this
Seventh Day of August, 2012

David J. Kappos
*Director of the United States Patent and Trademark Office*